United States Patent [19]

Crockard

[11] Patent Number: 5,174,276
[45] Date of Patent: Dec. 29, 1992

[54] ENDOSCOPE DEVICE FOR APPLYING AN ANEURYSM CLIP

[75] Inventor: Alan Crockard, Highgate, England

[73] Assignee: Hillway Surgical Limited, London, England

[21] Appl. No.: 689,802

[22] PCT Filed: Nov. 20, 1989

[86] PCT No.: PCT/GB89/01389
§ 371 Date: Jun. 28, 1991
§ 102(e) Date: Jun. 28, 1991

[87] PCT Pub. No.: WO90/05491
PCT Pub. Date: May 31, 1990

[30] Foreign Application Priority Data
Nov. 18, 1988 [GB] United Kingdom ........... 8826986

[51] Int. Cl.⁵ .................................... A61B 1/00
[52] U.S. Cl. ............................ 128/4; 604/95;
604/171; 604/280; 606/1; 606/142
[58] Field of Search ............... 606/143, 142, 1;
604/95, 158, 159, 164, 171, 280, 283, 156; 128/4

[56] References Cited

U.S. PATENT DOCUMENTS

| | | | |
|---|---|---|---|
| 3,162,214 | 12/1964 | Bazinet, Jr. ................... | 138/120 |
| 3,557,780 | 1/1971 | Sato ............................... | 128/4 |
| 3,870,048 | 3/1975 | Yoon ............................. | 128/4 X |
| 4,078,555 | 3/1978 | Takahashi ..................... | 128/4 |
| 4,203,430 | 5/1980 | Takahashi ..................... | 128/4 |
| 4,290,421 | 9/1981 | Siegmund ..................... | 128/6 |
| 4,351,323 | 9/1982 | Ouchi et al. .................. | 128/4 |
| 4,483,326 | 11/1984 | Yamaka et al. ............... | 128/4 |
| 4,624,254 | 11/1986 | McGarry et al. .............. | 606/143 |
| 4,655,257 | 4/1987 | Iwashita ........................ | 138/120 |
| 4,714,075 | 12/1987 | Krauter et al. ................ | 128/4 |
| 4,718,407 | 1/1988 | Chikama ....................... | 128/4 |
| 4,779,612 | 10/1988 | Kishi ............................. | 128/6 |

FOREIGN PATENT DOCUMENTS

| | | |
|---|---|---|
| 0165718 | 12/1985 | European Pat. Off. . |
| 0301288 | 2/1989 | European Pat. Off. . |
| 0301982 | 2/1989 | European Pat. Off. . |
| 1231015 | 5/1971 | United Kingdom . |

*Primary Examiner*—Stephen C. Pellegrino
*Assistant Examiner*—Jeffrey A. Schmidt
*Attorney, Agent, or Firm*—Flynn, Thiel, Boutell & Tanis

[57] ABSTRACT

A device for applying an aneurysm clip includes a novel lockable steerable endoscope (12), having steering mechanism (14), and a novel surgical device for applying the clip including an applicator (22) for the clip (24) comprising a remote actuator in the form of a flexible shaft (44) inside a flexible conduit (42), both running inside the endoscope, and jaws for holding the clip at the distal end of the shaft. The endoscope is steered to the site of the aneurysm and locked in position. The applicator is introduced into the endoscope, and moved to the site of the aneurysm by driving both the shaft and the conduit by drive mechanisms in the housing (20). The clip, when in position around the aneurysm, is actuated by movement of the shaft out of the conduit to open the jaws and release the clip which closes around the aneurysm.

16 Claims, 7 Drawing Sheets

FIG. 9b sites within the body to which access is difficult. For example, acces to aneurysms on blood vessels, particularly those at the base of the brain, is often very difficult. Aneurysms are treated by placing clips across their necks to isolate them from the blood vessel on which they have formed. This operation is currently performed by holding a clip open in a pair of specially adapted, rigid, forceps, and then positioning the clip around the neck of the aneurysm, and releasing it from the forceps by manual action. The rigidity of the forceps presents problems in the confined spaces within the brain, as a large arm movement by the surgeon may be required in order to effect a small movement of the tip of the instrument. Inaccuracies in movement and hand tremor can result in accidental damage to tissues and blood vessels. This is clearly especially undesirable when operating close to brain tissue.

ENDOSCOPE DEVICE FOR APPLYING AN ANEURYSM CLIP

The invention relates to surgical devices. Surgical devices according to the invention are especially useful for neurosurgery.

In many surgical techniques it is necessary to introduce instruments into the body, and to operate them at sites within the body to which access is difficult. For example, acces to aneurysms on blood vessels, particularly those at the base of the brain, is often very difficult. Aneurysms are treated by placing clips across their necks to isolate them from the blood vessel on which they have formed. This operation is currently performed by holding a clip open in a pair of specially adapted, rigid, forceps, and then positioning the clip around the neck of the aneurysm, and releasing it from the forceps by manual action. The rigidity of the forceps presents problems in the confined spaces within the brain, as a large arm movement by the surgeon may be required in order to effect a small movement of the tip of the instrument. Inaccuracies in movement and hand tremor can result in accidental damage to tissues and blood vessels. This is clearly especially undesirable when operating close to brain tissue.

According to a first aspect of the invention there is provided a deformable conduit comprising a plurality of conduit elements disposed end to end to form a conduit; at least two elongate tension members anchored to the conduit element at one end of the conduit and passing through each other conduit element successively; means for tensioning the tension members to cause adjacent conduit elements to bear and lock against each other and so render the conduit rigid; and a housing from which the conduit elements extend, the housing having an opening in each of two opposed walls; characterised in that the conduit further comprises a hollow shaft extending in the housing from one opening toward the other, the conduit elements being co-extensive with the shaft and passing through the said other opening; and a brake associated with each tension member which can bear on the tension member and so urge it against the element to hold the member against movement relative to the element.

It is particularly preferred that the deformable conduit is part of a conventional steerable endoscope of the otherwise conventional design, in which case the invention is particularly useful in neurosurgery. The endoscope can be introduced into sites which are normally difficult to gain access to with the minimal exposure of brain tissue, and when in position can be made rigid so that no unwanted movements of the endoscope tube take place.

According to a second aspect of the invention there is provided a remote actuator comprising: a conduit; a shaft axially movable within the conduit; a drive for driving the conduit and the shaft along their axes which can be disengaged from at least one of them; and actuation means for moving axially either the conduit or the shaft, for actuation whereby, in use, the conduit and shaft can be moved as one to position the actuator, and relative to one another for actuation.

Preferred embodiments of the second aspect of the invention provide a surgical device, for introducing a surgical instrument to an operating site in a patient and actuating the instrument, comprising: a conduit; a shaft axially movable within the conduit; a first drive to drive the conduit in an axial direction; a second drive operably connected to the first drive to drive the shaft in an axial direction, at least one of the first and second drives being movable into and out of engagement with the conduit or shaft respectively, so that the shaft and conduit can be driven as one and one another of them can be driven alone. The end of the device distant from the drives being adapted to carry a surgical instrument actuable by relative axial movement of the conduit and the shaft whereby, in use, the distal end of the device can be introduced into a patient and moved by the first and second drives to an operating site where the instrument can be actuated by the relative movement of the conduit and the shaft.

Preferably, a third drive is provided, operable independently of the first and second drives to drive only one of the conduit and the shaft in the axial direction, to effect relative movement of the conduit and the shaft.

The surgical device of the invention is useful when used within a tube, such as an endoscope, which itself is introduced into the body either through a natural orifice or an incision, and particularly useful when used with a conventional steerable endoscope. The surgical device is particularly useful when used with a deformable tube endoscope according to the first aspect of the invention. In this case, it is particularly advantageous that the conduit and shaft of the surgical device of the invention be flexible.

In employing the devices of the invention together with a steerable endoscope, only a small hole need be made in the skull or body tissue of the patient in order to introduce the endoscope. Normally, when a surgical device of the invention is used in surgery on the cranium, the proximal ends of the device and associated endoscope will be mounted on a halo-type mounting around the patient's skull. This holds the surgical device and the endoscope immobile relative to the skull of the patient, reducing the risk of damage by unwanted movement of the device or endoscope.

A surgical instrument attached to the distal tip of the device of the invention can be carried to the sites to be operated on through the ventricles of the brain or around the base of the brain.

Introducing surgical instruments using a steerable endoscope in this way allows an operation to be performed using far less potentially damaging techniques than are used at present. For example, if an instrument were to be introduced around the brain for the occlusion of a basilar aneurysm using the invention in conjunction with and endoscope, less retraction of the brain and less exposure of the brain tissue would be necessary than is the case with present techniques.

The tip of the steerable endoscope is controlled remotely, so that when the device of the invention is used with an endoscope of this type, movement to close to the final position of the distal tip of the device is not subject to the hand tremor associated with hand held instruments. The tip of the surgical device of the invention may then be advanced and retracted smoothly to and from the exact site of the operation, by use of the first and second drive means, again without hand tremor. Actuation of the surgical instrument is achieved by use of the third drive means, which either extends the shaft within the conduit, or retracts the conduit over the shaft, to actuate the instrument. Whilst actuation is being effected, one or both of the first and second drive means is disengaged from either the conduit or the shaft or both, so that the surgical device as a whole does not extend further or retract. Optical fibres may be introduced into the endoscope, allowing direct viewing of the area operated upon. This assists in very accurate positioning of the instrument.

According to a third aspect of the invention there is provided an applicator for applying an aneurysm clip to a blood vessel at a site within a patient's body, comprising a shaft axially movable within a conduit and jaws adapted to hold an aneurysm clip disposed at an end of the shaft, the jaws being resiliently biased to the open position and movable by axial movement of the shaft relative to the conduit between a closed condition in which the jaws are restrained against opening by the conduit wall and an open condition in which the jaws are free of the conduit.

In preferred aneurysm clip applicators according to the third aspect of the invention, the shaft and conduit are part of a surgical device according to the second aspect of the invention.

This aspect of the invention is envisaged to be particularly useful in the clipping of aneurysms in the cranium, but may also be used with advantage in otherr relatively inaccesible areas of the body.

The invention also contemplates, in a fourth aspect, a kit for clipping aneurysms comprising a steerable endoscope according to the first aspect of the invention the preferred applicator according to the third aspect of the invention.

The invention will be further described by way of example with reference to the drawings in which.

Figure 1:
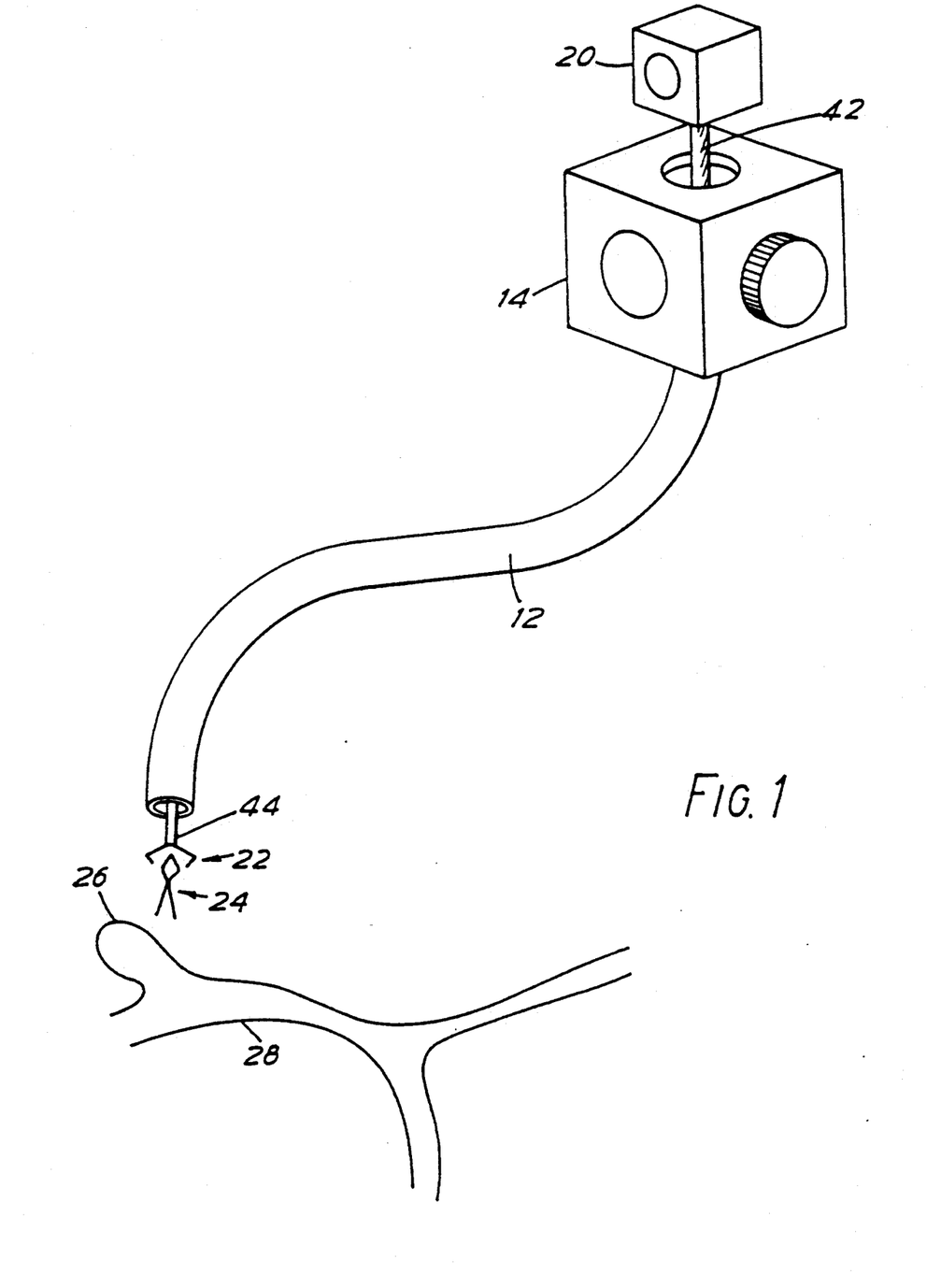
FIG. 1 is a perspective view of a device for applying an aneurysm clip embodying the invention.

The device of FIG. 1 includes a steerable endoscope tube 12 with a remote steering mechanism 14 of known type. A flexible conduit 42 of a surgical device according to the invention is positioned and axially movable in the endoscope tube, and a shaft 44 is positioned and axially movable in the conduit. Movement of the conduit and shaft together or with respect to one another is controlled by a mechanism housed in housing 20, which will be described in greater detail below. At the distal tip of the shaft is an aneurysm clip applicator 22 for applying an aneurysm clip 24 of conventional type to an aneurysm 26 in a blood vessel 28. Actuation of the applicator 22 will be further described in detail below.

Figure 2A:
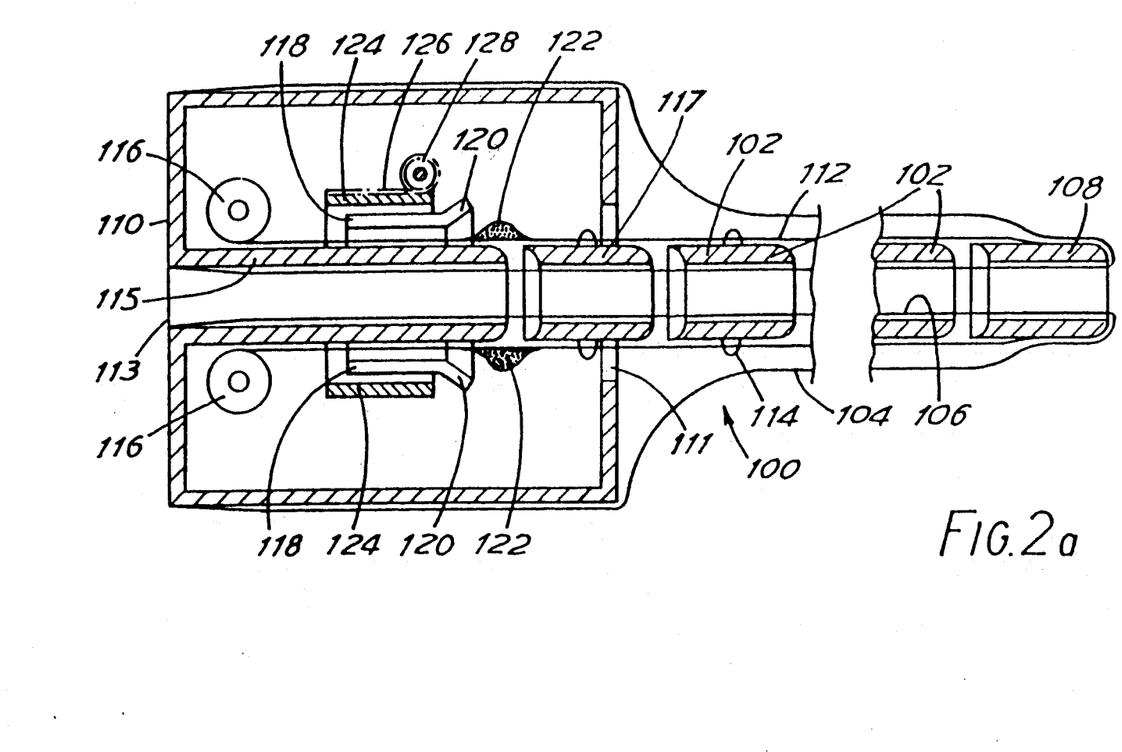
FIGS. 2a, b and c show diagrammatic sections of an endoscope according to the first aspect of the invention.
Figure 2B:
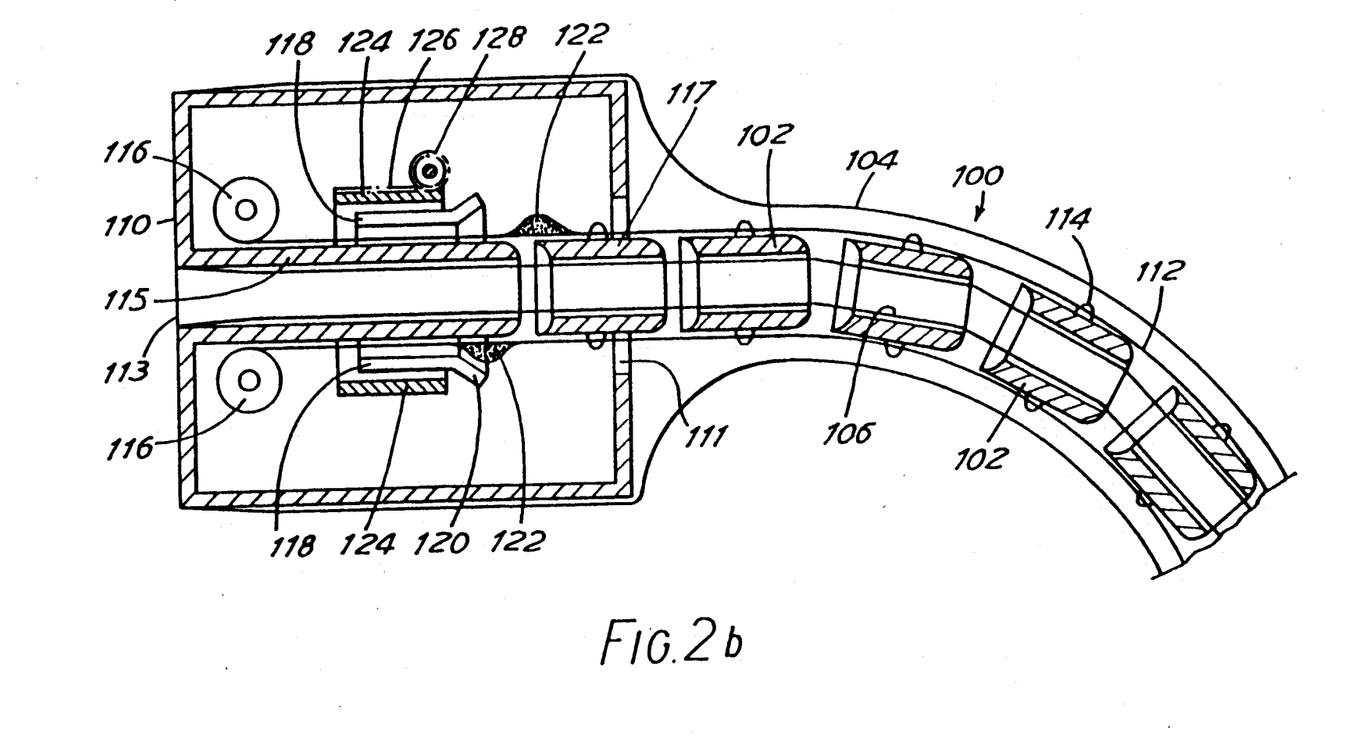
Figure 2C:
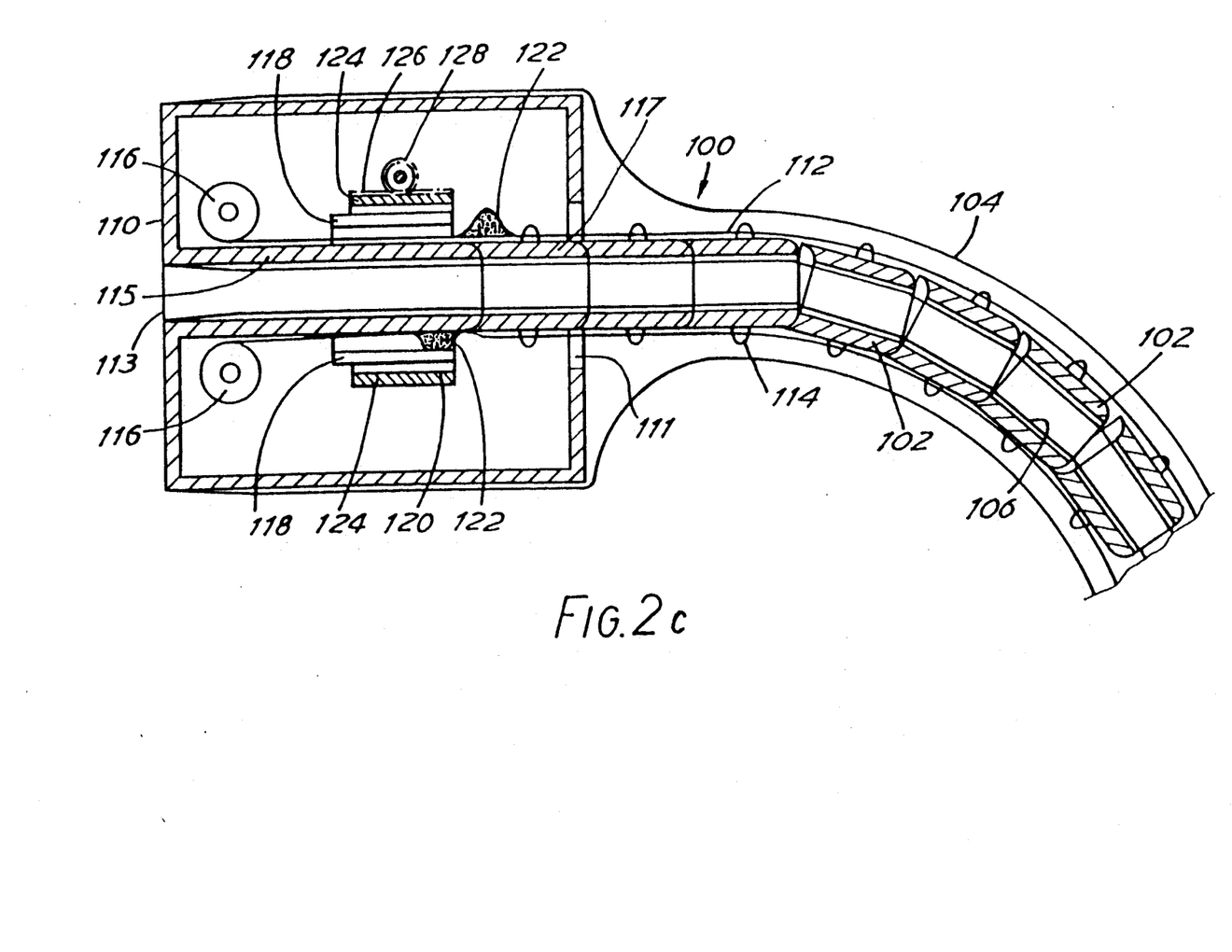

An embodiment of the first aspect of the invention is shown in FIG. 2a, b and c. The endoscope of this embodiment is steerable, by conventional means (not shown). It includes a deformable endoscope tube 100 made up of a plurality of relatively short tubular endoscope elements 102 articulated end to end. A flexible sleeve 104 of a sterilisable plastics material covers the endoscope tube 100, and a liner 106 also of a sterilisable plastics material lines the tube. The sleeve 104 and liner 106 are affixed to the distal end endoscope element 108, as shown in FIG. 2a. The sleeve and liner are formed of a single piece of plastics material, and extend continuously over the outer and inner surfaces of the endoscope tube 100.

The distal end of the endoscope tube 100 is free, while the proximal end is held in a housing 110. The end of the flexible sleeve 104 is affixed to the outside of the housing which has provision for clamping it to a halo-type frame or other anchoring.

The housing has a first opening 111 in one wall to admit the endoscope tube 100. The opposite wall has a second opening 113 to allow access to the tube 100. A hollow stem 115 extends from the second opening 113 toward the first opening 111. The proximal end endoscope element 117 abuts the end of the stem 115. The liner 106 is affixed to the inner surface of the stem 115. The diameter of the endoscope tube 100 is large enough to allow several instruments to be admitted.

The conduit elements 102 are joined together by three tension wires 112 of which two are shown in FIG. 2. One tension wire may be omitted, or further tension wires used, if desired. The tension wires 112 pass through eyes 114 on the outer surface of each conduit element 102. Alternatively, the tension wires can pass through channels in the conduit element. An end of each tension wire 112 is attached to the spindle of a spring motor 116.

The spring motor 116 is of conventional type, consisting of a helically wound spring (not shown), the inner end of which is attached to the spindle of the motor and the outer end of which is attached to the housing 110. The spring motors 116 operate to maintain a constant tension in the wires 112 as the endoscope is steered to the site of the operation. The spring motors will normally be identical to each other, to ensure that all tension wires 112 are under substantially the same tension.

A brake is provided to hold the wires 112 immobile, and so under constant tension. The brake is in the housing 110. The brake comprises for each wire 112, a brake plate 118 in the form of a curved metal plate extending partly around the stem 115 in the housing 110, over the wire 112. A marginal portion 120 of the plate 118 is resiliently biased away from the stem 115. A thicker length 122 of the wire 112 underlies the resiliently biased portion of the plate 118.

An actuating sleeve 124 overlies the brake plates 118. The sleeve has a rack 126 on its outer surface engaged by a toothed wheel 128. The wheel is mounted on an axle (not shown) and may be turned by a knurled wheel also mounted on the axle, externally of the housing 110.

By manual rotation of the knurled wheel, the toothed wheel 128 causes the actuating sleeve 124 to move against the resiliently biased marginal portion 120 of the brake plates 118, to urge them against the thicker lengths 122 of the wires 112, and so hold the wires between the plates 118 and the outer surface of the stem 115 to prevent movement of the wires. The plates 118 can be locked in the 'on' condition by means not shown, manually engagable and disengageable such as a lock preventing rotation of the axle upon which the toothed wheel 128 is mounted.

Figure 3:
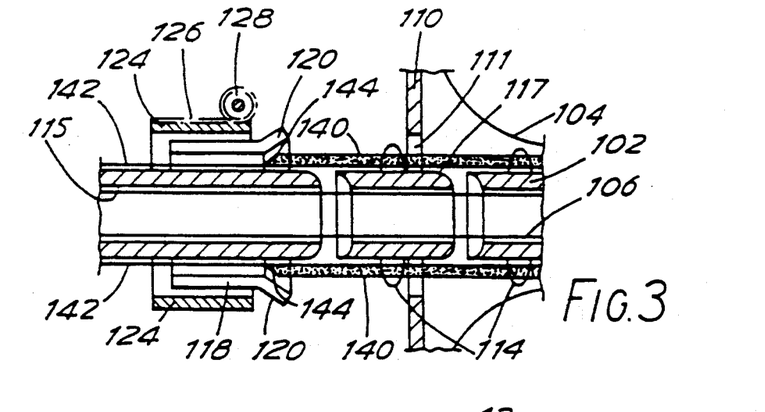
FIG. 3 shows a diagrammatic section of part of a second embodiment of an endoscope according to the first aspect of the invention.

In a second embodiment shown in FIG. 3, the tension members are flexible plastic cables 140 which are relatively thick, for example 2-3 mm in diameter. The plastic cables 140 have at their proximal ends a thinner portion 142. The thick and thin portions are connected at a tapered face 144, which generally underlies the brake plate 118.

In this embodiment, when the tube is bent, one of the thick portions of the cables 140 moves further under the end of the brake plate 118. When the brake is applied, the marginal portion 120 of the brake plate 118 bears on the tapered face 144 of the cable 140, to hold the cable against movement.

Another alternative brake, not shown, comprises for each wire a cam member pivotable, by a lever or wheel external to the housing 110 and operably connected to the cam member. The cam member is pivotable between a first, off, position in which the cam is out of contact with the wire, and a second, on, position in which the cam member bears on the thicker length 122 of the wire 112 to hold it against the outer surface of the stem 115.

In use, the endoscope is introduced into the patient's body and driven to the site to be operated upon in a conventional manner.

FIG. 2b shows this position, with the tube 100 bent as it enters the patient's body (not shown).

When the distal end of the endoscope tube 100 is at the site of the operation, the tension wires 112 are tensed to draw each conduit element 102 into contact with adjacent elements, so that their end surfaces grip. This holds the tube 100 rigid, as shown in FIG. 2c to hold the configuration, and keep the tube 100 rigid, the brake is operated, so that the tension in the wires is maintained.

The tension is applied to the wires 112 by turning the spindles of the spring motors 116 to wind the wires into the spindles. It is desirable that all the tension wires 112 are under about the same tension, and so desirably a single handle (not shown) is operably connected, in one of many well known ways, to each spindle, to turn them together.

The tension in the wires can be relaxed by turning in the opposite direction the handle which turns the spindles of the spring motors 116 so the tube is then flexible once more. When the tube bends, as it is steered, any slack in one of the wires 112 is taken up by the respective spring motor 116.

This aspect of the invention thus provides an endoscope which may be moved to an operation site easily, since it is flexible. When in position, it may be rendered rigid, so that movement of the proximal end causes little disturbance at the distal end. The surgical device and the aneurysm clip applicator of the second and third aspects of the invention may be used with the advantage in conjunction with the endoscope of the first aspect. Instruments other than the aneurysm clip applicator may be used, and it is envisaged that the invention will be useful in many other operations, such as intraventricular surgery, posterior fossa surgery, pituitary surgery, choroid plexeotomy and biopsy excision. Examples of instruments which could be used in an endoscope according to the invention are instruments for suction irrigation, visual inspection of the operation site and laser treatment and biopsy forceps.

Figure 4:
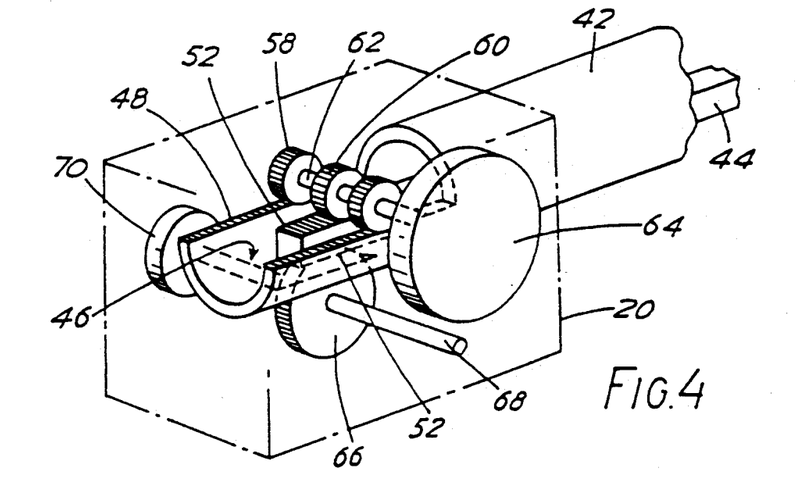
FIG. 4 is a diagrammatic perspective view of one end of a first embodiment of a surgical device according to the second aspect of the invention.
Figure 5:
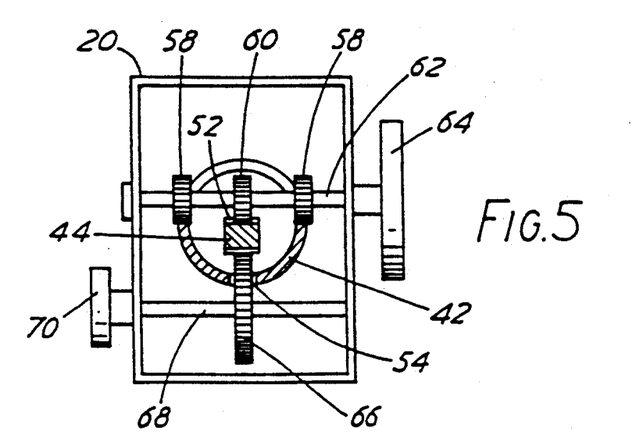
FIG. 5 is a section through the device of FIG. 4.

The proximal end portion of a preferred surgical device is shown in FIGS. 4 and 5. The distal portion of the device is omitted for clarity.

The conduit 42 and shaft 44 extend into a housing 20. The end portion of the conduit 42 is partly cut away to form a channel 46 in which the end portion of the shaft 44 lies. The conduit 42 is of circular section, and the shaft 44 is of square section.

The faces of the side walls of the channel 46 each have a rack 48 of teeth extending axially along the channel, and the end portion of the shaft 44 has a rack 52 of teeth extending axially along the surface exposed in the channel. The base of the channel 46 has a slot cut in it, and a rack 52 extends axially along the surface of the shaft 44 opposite the slot 54.

A pair 58 of first driving wheels and an intermediate second driving wheel 60 are mounted on a first axle 62 extending through the housing 20 transversely to the conduit and shaft. The wheels have teeth on their outer rim, and are disposed and dimensioned so that the pair of first driving wheels can engage the rack on the channel portion 46 of the conduit 42 while, at the same time, the second wheel 60 engages the rack 52 on the exposed surface of the shaft 44. The axle 62 has a knurled wheel 64 mounted on it externally of the housing 20.

By rotation of the knob 64, the first and second driving wheels are rotated to move both the conduit 42 and the shaft 44 together in the axial direction. The gearing between the wheels and the conduit and shaft are chosen so that the shaft and conduit move together at the same velocity as each other.

By sliding the axle 62 transversely across the housing, the wheels may be moved out of engagement with the racks on the conduit and shaft.

A third driving wheel 66, also mounted on a second axle 68 extending transversely through the housing 20, passes through the slot 54 so that teeth on the rim of the wheel engage the rack 56 on the surface of the shaft 44 opposite the slot.

A knurled knob 70 is mounted on the second axle 68 externally of the housing 20. By rotation of the knurled knob 70, the third wheel 66 is caused to rotate, and so moves the shaft 44 axially within and relative to the conduit 42. Provided that the first axle 62 carrying the first 58 and second 60 driving wheels is in the disengaged position, no movement of the conduit will be occasioned by movement of the shaft 44.

Figure 6:
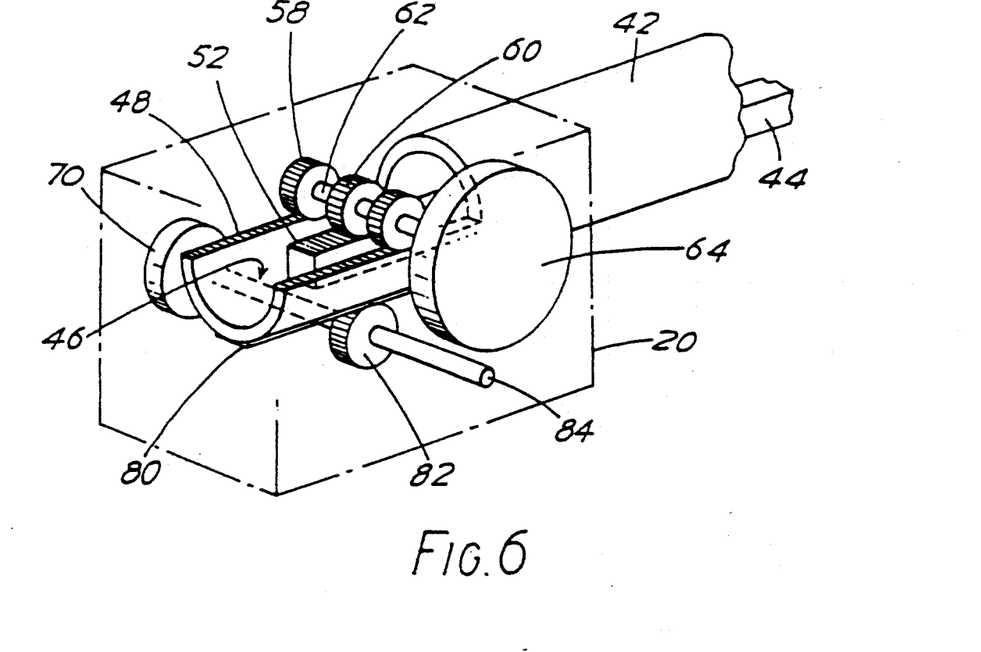
FIG. 6 is a diagrammatic perspective view of a second embodiment of a surgical device according to the second aspect of the invention.
Figure 7:
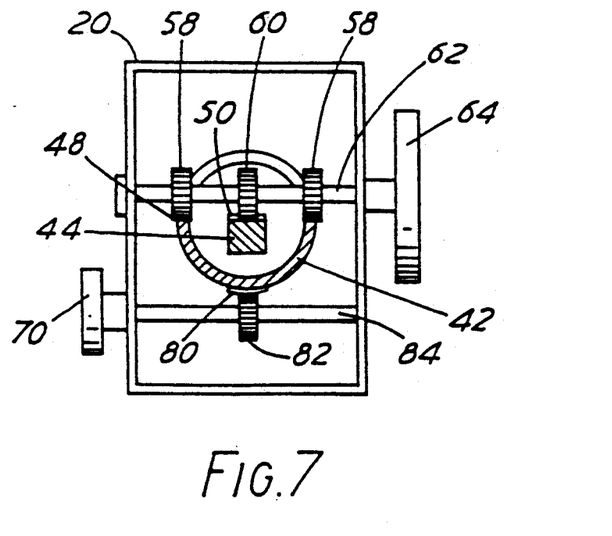
FIG. 7 is a section through the device of FIG. 4.

In the second preferred embodiment of a surgical device according to the invention, a different driving arrangement is employed. This arrangement is shown in FIGS. 6 and 7. In this embodiment, the conduit 42 and coaxial shaft 44 are mounted in a housing 20 as in the first embodiment. Also as in the first embodiment, a channel portion 46 of the conduit 42 is formed by a cutaway at the end portion of the conduit within the housing 20. As in the first preferred embodiment, the end faces of the side walls of the channel 46 and the exposed surface of the shaft 44 are each provided with an axially extending rack of teeth 48, 50 respectively. A pair 58 of first and the second 60 driving wheels are disposed on a first axle 62 identically with the first embodiment. The first and second driving wheels have teeth on their rims, and are operable to move the conduit 42 and shaft 44 together as in the first embodiment, and can be moved out of engagement with the racks on the conduit and shaft.

In this embodiment, there is no slot in the base of the channel portion 46 of the conduit 42. The outer surface of the base of the channel portion 46 of the conduit 42 has a rack 80 of teeth disposed axially upon it. A third driving wheel 82 mounted on a second axle 84 extending transversely across the housing 20 engages with the rack 80 on the outer surface of the base of the channel portion 46.

When it is desired to move the conduit relative to the shaft, the first axle 62 is moved so that the first 58 and second 60 driving wheels are out of engagement with their respective racks 48, 50 on the conduit 42 and shaft 44, and a knurled wheel 70 mounted externally of the housing 42 on the second axle 84 which carries the third driving wheel 82 is turned to rotate the driving wheel 82 and thus the conduit 42.

Referring again to FIG. 1, the conduit 42 and shaft 44 of a surgical device according to the invention may be inserted into a steerable endoscope 12, which itself can be inserted into the body of a patient, either through a natural orifice or through an incision. In the case of neurosurgery, access will normally be gained by means of an incision and a small hole in the skull. The steerable endoscope may be mounted on a halo type frame surrounding the patient's head, and the control housing of the surgical device may be similarly mounted, to guard against unwanted movement.

The distal end of the steerable endoscope 12, containing the distal end of the surgical device of the invention, is introduced into the incision, and moved close to the site of the operation in a conventional manner, such as manually, or by steering in the case of a conventional steerable endoscope. When the site of the operation is almost reached, the endoscope is held in position and the conduit 42 and shaft 44 are moved together to the exact site of the operation by turning the first knurled wheel 64 to move the conduit 42 and shaft 44 together. When the instrument carried by the device is in position, it may be actuated by relative movement of the shaft and conduit, achieved by rotation of the second knurled wheel 70 to move either the shaft alone or the conduit alone.

Figure 8A:
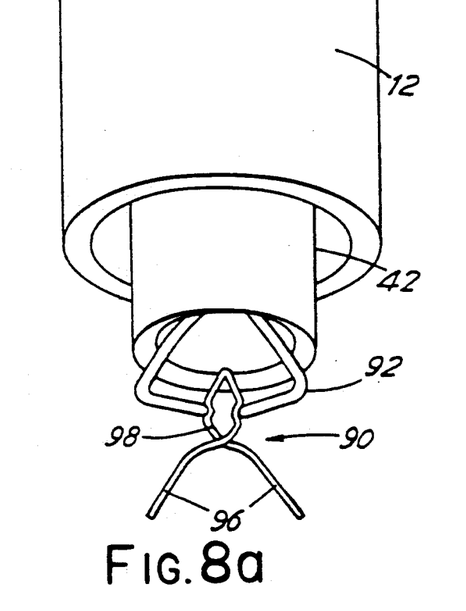
FIGS. 8a and b are diagrammatic perspective views of an embodiment of an aneurysm clip applicator according to the third aspect of the invention.

The surgical device of the invention finds particular application when used with the novel design of aneurysm clip applicator described below, with reference to FIGS. 8 and 9. FIGS. 8a and b show stages in the application of an aneurysm clip 90 to an aneurysm (not shown). FIGS. 9a and b are sectional views of FIGS. 8a and b.

The aneurysm clip applicator comprises jaws 92 pivotally mounted on a stem 94, itself attached to the distal end of the shaft 44 of the surgical device of either of the types shown in FIGS. 4-7. The jaws 92 of the applicator are resiliently biased to the open position, shown in FIGS. 8b and 9b.

When the applicator is withdrawn inside the conduit 42 of the surgical device, as shown in FIGS. 8a and 9a, the jaws are closed, since they are restrained against opening by the internal wall of the conduit 42. In use, an aneurysm clip 90 is held in the jaws 92 of the aneurysm applicator, which is then introduced by means of a steerable endoscope 12 to a position close to the site of the aneurysm.

Conventional aneurysm clips 90 comprise two legs 96, which are resiliently biased towards each other, to close the aneurysm when they are in position. The legs 96 of the clip cross and curve round to join each other to form a loop, the handle 98 of the clip 90. It will be appreciated that when the handle loop 98 is squeezed closed, the legs 96 move apart, and that when the handle is released, the resilience of the clip causes the legs 96 to move together.

When the aneurysm clip 90 is held in the closed jaws 92 of the aneurysm clip applicator, as shown in FIGS. 8a and 9a, the handle 98 is held between the jaws, causing the legs 96 to open. The applicator is introduced to the site of the aneurysm down the endoscope 12, and moved into exact position, with the legs 96 either side of the neck of the aneurysm, by rotation of the first knurled wheel 64, to move the conduit 42 and the shaft 44 together into position.

Figure 8B:
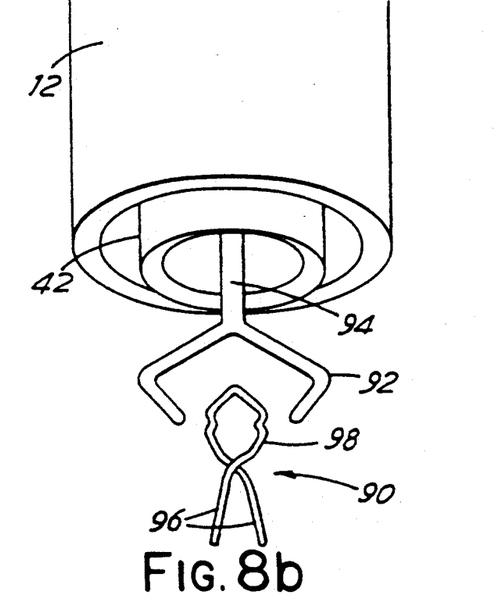
Figure 9A:
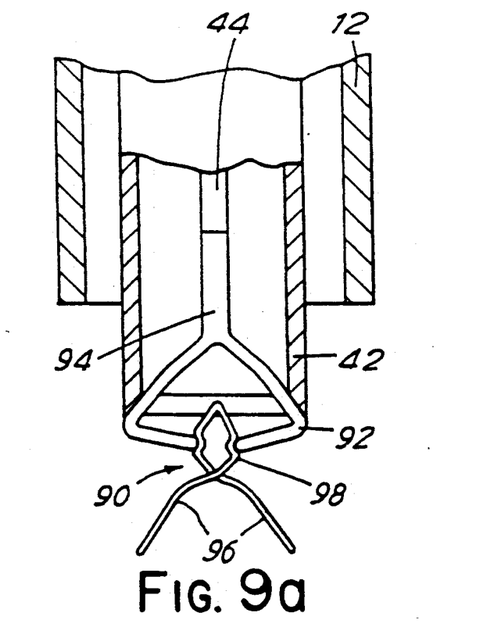
FIGS. 9a and b are sections through the applicator of FIGS. 8a and b.
Figure 9B:
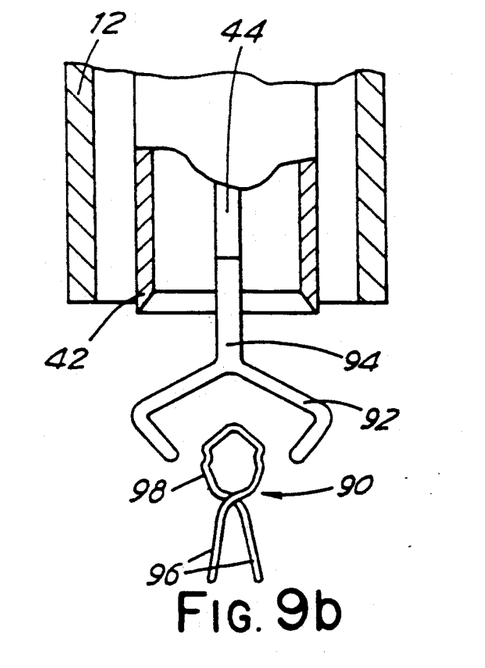

When the clip is in position, the jaws are released by operation of the second knurled wheel 70 to move the shaft relative to the conduit, as shown in FIGS. 8b and 9b. It will be appreciated that when the first embodiment of the surgical device, shown in FIGS. 4 and 6 is employed, in which relative movement of the shaft and the conduit is achieved by movement of the shaft, the aneurysm clip applicator will be actuated to open the jaws 92 a short distance away from the eventual site of the aneurysm clip, since a little further movement of the jaws and the clip takes place during actuation. In the case of the second embodiment, shown in FIGS. 4 and 5 in which the conduit is withdrawn slightly to effect actuation of the applicators, the clip is placed in the precise position required, around the neck of the aneurysm, immediately prior to actuation.

If the clip is applied slightly out of the desired position, the jaws can be closed around it by operation of the second knurled wheel 70 in the opposite direction to that employed to apply the clip. The applicator may then be repositioned by use of knurled wheel 64, and actuated once more to release the clip around the aneurysm.

The distal end faces of the conduit 42 are bevelled inwards to ensure the smooth operation of the jaws 92 as they move in and out of the conduit 42.

The endoscope 12 advantageously carries fibre optics to enable the surgeon operating the aneurysm clip applicator to see the site of the operation. Other surgical instruments may also be introduced into the endoscope 12 to assist in the operation.

I claim:

1. A deformable conduit comprising a plurality of conduit elements disposed end to end to form a conduit; at least two elongate tension members anchored to a conduit element at a distal end of the conduit and passing through each conduit element successively; a spring motor associated with each tension member at a proximal end of the conduit, each spring motor having a spindle and one end of the respective tension member being attached to the spindle of the respective spring motor for tensioning the tension members to cause adjacent conduit elements to bear and lock against each other and so render the conduit rigid; and a housing at the proximal end of the conduit from which the conduit elements extend, the housing having an opening in each of two opposed walls; characterized in that the conduit further comprises a hollow shaft extending in the housing from one opening toward the other opening, the conduit elements being coextensive with the shaft and passing through said other opening; and a brake associated with each tension member which can bear on the tension member and so urge it against the shaft to prevent the tension member from moving relative to the shaft.

2. A deformable conduit according to claim 1 in which there are three tension members disposed substantially evenly around the conduit.

3. A deformable conduit according to claim 1 in which each brake comprises a plate extending partially around the shaft and the respective tension member, at least a portion of the plate being resiliently biased away from the tension member and shaft, and a brake actuator movable between a position in which the plate bears on the tension member and so urges it against the shaft and an off position in which the plate does not bear on the tension member.

4. A deformable conduit according to claim 3 in which the broke actuator is a sleeve extending around the shaft and movable from an on position in which the sleeve lies over the plate and biases it toward the shaft to bear on the tension member and an off position in which the sleeve does not lie over the plate.

5. A deformable conduit according to claim 1 in which the brake is a cam rotatable between an on position in which it bears on the tension member to urge it against the shaft and an off position in which it does not bear on the tension member.

6. A steerable endoscope comprising a deformable conduit, the deformable conduit comprising a plurality of conduit elements disposed end to end to form a conduit; at least two elongate tension members anchored to a conduit element at a distal end of the conduit and passing through each conduit element successively; a spring motor associated with each tension member at a proximal end of the conduit, each spring motor having a spindle and one end of the respective tension member being attached to the spindle of the respective spring motor for tensioning the tension members to cause adjacent conduit elements to bear and lock against each other and so render the conduit rigid; and a housing at the proximal end of the conduit from which the conduit elements extend, the housing having an opening in each of two opposed walls; characterized in that the conduit further comprises a hollow shaft extending in the housing from one opening toward the other opening, the conduit elements being coextensive with the shaft and passing through said other opening; and a brake associated with each tension member which can bear on the tension member and so urge it against the shaft to prevent the tension member against moving relative to the shaft.

7. A surgical device for introducing a surgical instrument to an operating site in a patient and actuating the instrument, comprising: a conduit; a shaft axially movable within the conduit; a first drive means to drive the conduit in an axial direction; a second drive means operably connected to the first drive means to drive the shaft in an axial direction, at least one of the first and second drive means being movable into and out of engagement with the conduit or shaft respectively, so that the shaft and the conduit can be driven as one or driven independently of each other, a third drive means operable independently of the first and second drive means to drive only one of the conduit and the shaft in the axial direction, whereby relative movement of the conduit and the shaft is effected to actuate the surgical instrument, the end of the device distal to the drive means being adapted to carry a surgical instrument which is actuatable by relative movement of the conduit and the shaft whereby, in use, the distal end of the device can be introduced into a patient and moved by the first and second drive means to an operating site where the instrument can be actuated by relative movement of the conduit and the shaft.

8. A surgical device according to claim 7 in which the conduit and the shaft are flexible.

9. A surgical device according to claim 7 in which each drive means comprises a rotatable toothed wheel and a rack disposed on the conduit or the shaft respectively which is engaged by the wheel.

10. A surgical device according to claim 9 in which the first drive means comprises two toothed wheels on a single axle and two racks on the conduit.

11. A surgical device according to claim 9 in which the toothed wheels of the first and second drive means are movable on a single axle between an engaged position in which the wheels are in engagement with their respective racks and a disengaged position in which they are out of engagement with their respective racks.

12. A surgical device according to claim 9 in which a region of the proximal end portion of the conduit is a channel exposing the shaft and the wheel of the first drive means engages a side wall of the channel and the wheel of the second drive means engages the shaft in the channel.

13. A surgical device according to claim 12 in which the wall of the channel has a slot through which the wheel of the third drive engages the shaft.

14. A surgical device according to claim 12 in which the wheel of the third drive means engages the base of the channel.

15. A surgical device according to claim 7 in which the drives are manually operable.

16. A kit for clipping aneurysms in a patient containing: (i) a steerable endoscope comprising: a deformable conduit comprising a plurality of conduit elements disposed end to end to form a conduit; at least two elongate tension members anchored to the conduit element at a distal end of the conduit and passing through each conduit elements to bear and lock against each other and so render the conduit rigid; and a housing at a proximal end of the conduit from which the conduit elements extend, the housing having an opening in each of two opposed walls; characterized in that the conduit further comprises a hollow shaft extending in the housing from one opening toward the other opening, the conduit elements being coextensive with the shaft and passing through said other opening; and a brake associated with each tension member which can bear on the tension member and so urge it against the shaft to prevent the tension member from moving relative to the shaft, and (ii) a surgical device for introducing a surgical instrument to an operating site in a patient and actuating the instrument, comprising: a conduit; a shaft axially movable within the conduit; a first drive means to drive the conduit in an axial direction; a second drive means operably connected to the first drive means to drive the shaft in an axial direction, at least one of the first and second drive means being movable into and out of engagement with the conduit or shaft respectively, so that the shaft and the conduit can be driven as one or driven independently of each other, a third drive means operable independently of the first and second drive means to drive only one of the conduit and the shaft in the axial direction, whereby relative movement of the conduit and the shaft is effected to actuate the surgical instrument, the end of the device distal to the drive means being adapted to carry a surgical instrument which is actuatable by relative movement of the conduit and the shaft whereby, in use, the distal end of the device can be introduced into a patient and moved by the first and second drive means to an operating site where the instrument can be actuated by relative movement of the conduit and the shaft.

* * * * *